United States Patent [19]

Mase et al.

[11] Patent Number: 4,505,783
[45] Date of Patent: * Mar. 19, 1985

[54] OXYGEN CONCENTRATION DETECTOR AND METHOD OF USING SAME

[75] Inventors: Syunzo Mase, Ama; Shigeo Soejima, Nagoya, both of Japan

[73] Assignee: NGK Insulators, Ltd., Japan

[*] Notice: The portion of the term of this patent subsequent to Oct. 4, 2000 has been disclaimed.

[21] Appl. No.: 380,282

[22] Filed: May 20, 1982

[30] Foreign Application Priority Data

May 25, 1981 [JP] Japan .................. 56/77923

[51] Int. Cl.³ .............................. G01N 27/46
[52] U.S. Cl. .................. 204/1 T; 204/412; 204/425; 204/426; 204/427; 204/429; 219/553
[58] Field of Search .................. 204/1 S, 421–429; 422/98; 219/505, 553

[56] References Cited

U.S. PATENT DOCUMENTS

| | | | |
|---|---|---|---|
| 3,924,098 | 12/1975 | Dunn | 219/553 |
| 4,101,454 | 7/1978 | Kulwicki et al. | 219/553 |
| 4,145,272 | 3/1979 | Nakamura | |
| 4,167,163 | 9/1979 | Moder | 204/424 |
| 4,224,113 | 9/1980 | Kimura et al. | 204/425 |
| 4,265,724 | 5/1981 | Haecker | |
| 4,293,838 | 10/1981 | Wahlers et al. | 219/553 |
| 4,298,573 | 11/1981 | Fujishiro | 204/426 |
| 4,304,652 | 12/1981 | Chiba et al. | 204/426 |
| 4,321,577 | 3/1982 | Carlson | 422/98 |
| 4,407,704 | 10/1983 | Mase et al. | 204/425 |

FOREIGN PATENT DOCUMENTS

| | | | |
|---|---|---|---|
| 0030164 | 6/1981 | European Pat. Off. | 204/427 |
| 0079246 | 6/1981 | Japan | 204/428 |

*Primary Examiner*—T. Tung
*Attorney, Agent, or Firm*—Parkhurst & Oliff

[57] ABSTRACT

An oxygen concentration detector comprises an oxygen ion conductive solid electrolyte body and electrodes provided thereon to form an oxygen concentration cell for detecting oxygen partial pressure in a gas such as exhaust gas from an internal combustion engine. The oxygen concentration detector according to the invention further comprises an AC power source supplying to the electrodes an AC current having a frequency at which a polarization of alternating current component is caused mainly due to a polarization of the solid electrolyte body to heat it, and a DC power source supplying a direct current to the electrodes so as to control oxygen concentration on the side of at least one electrode of the oxygen concentration cell to detect its electromotive force.

21 Claims, 22 Drawing Figures

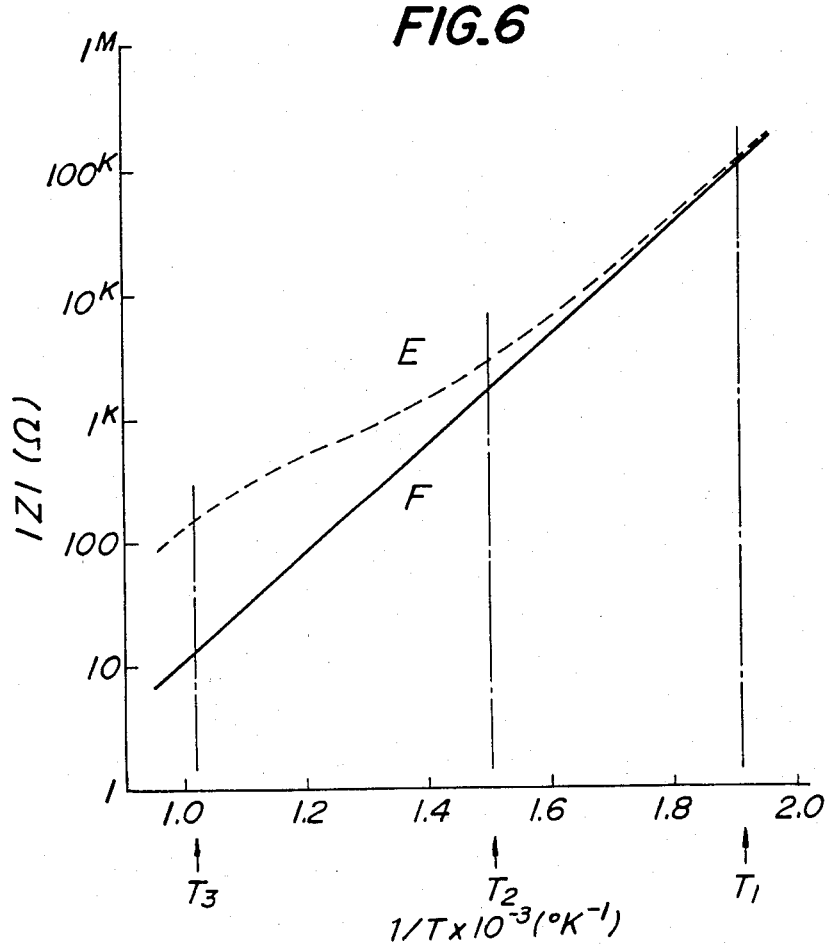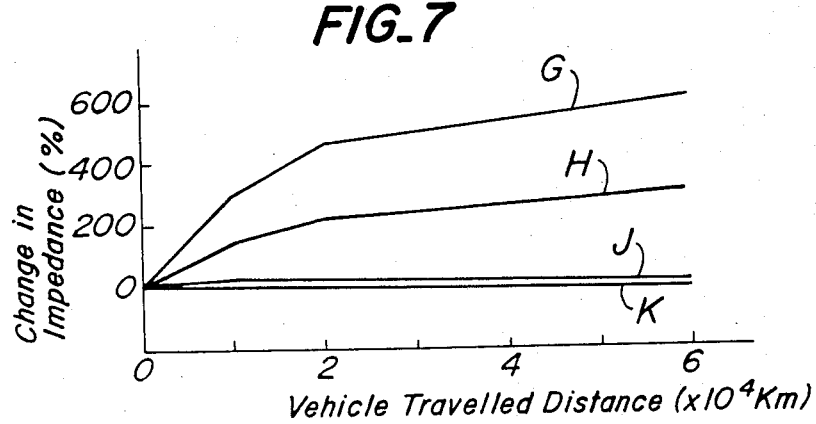

OXYGEN CONCENTRATION DETECTOR AND METHOD OF USING SAME

BACKGROUND OF THE INVENTION

1. Field of the Invention

This invention relates to an oxygen concentration detector for detecting oxygen concentration of a gaseous mixture with an oxygen concentration cell using an oxygen ion conductive solid electrolyte body.

2. Description of the Prior Art

To measure the oxygen concentration of the exhaust gas from an internal combustion engine or the like, an oxygen concentration detector having an oxygen ion conductive solid electrolyte body and based on the principle of an oxygen concentration cell has been known. The oxygen concentration detector of the prior art generally comprises a solid electrolyte body made of, for example, yttria added zirconia ceramic and electrodes made of platinum. Such an oxygen concentration detector has been usually used for controlling air-fuel ratio $\lambda$ to maintain it at 1.0. However, it is often necessary to control the air-fuel ratio $\lambda$ to values other than 1.0 in order to use the engine in a lean burn zone including much air for higher fuel efficiency or a rich burn zone including less air for higher output efficiency. For this purpose, it is also necessary to precisely measure the electromotive force of the oxygen concentration cell and temperature.

Various oxygen concentration detectors simultaneously measuring the temperature and electromotive force have been proposed. For example, as shown in FIG. 1, a solid electrolyte body 1 in the form of a bottomed cylinder having electrodes 5 and 4 on its inner and outer surfaces includes a temperature sensor element 2 therein for measuring the temperature of the solid electrolyte body 1 or a coiled heating wire 3 therein for heating the solid electrolyte body 1 or includes simultaneously a temperature sensor element 2 and coiled heating wire 3 for heating the body and detecting the temperature thereof. These detectors could not precisely measure the temperature of the solid electrolyte body because they detect temperatures only at one point notwithstanding the temperature of the solid electrolyte body exposed to exhaust gases of an internal combustion engine is not uniform. Moreover, when the temperature of the exhaust gas varies, the temperature sensor element could not immediately respond to the change in temperature of the solid electrolyte body resulting in delayed output of the temperature detector element. In addition, with these oxygen concentration detectors, at low temperatures the catalytic action of the platinum become lower and the electric resistance of the solid electrolyte body itself becomes higher in response to increase of impedance of the detectors, so that they are susceptible to noise and tend to delay in response, with the result that they are in practise useless in conjunction with their complicated construction.

Furthermore, it has been proposed to vary the air-fuel ratio to values other than 1.0 causing a change in electromotive force by flowing a direct current in an oxygen concentration cell. However, this method could not precisely detect the temperature because of its great intensity of polarization at low temperatures and of great variation in excess-air ratio $\lambda$ depending upon temperatures.

SUMMARY OF THE INVENTION

It is an object of the invention to provide an improved oxygen concentration detector which eliminates such disadvantages of the prior art and which is capable of stably controlling air-fuel ratio $\lambda$ for a long time usage and exhibits a high responsibility even at low temperatures.

In order to accomplish the object, the oxygen concentration detector according to the present invention comprises an alternating current power source for applying to said electrodes provided on said solid electrolyte body an alternating voltage so as to flow an alternating current having a frequency at which a polarization of alternating current component is caused mainly due to a polarization of said solid electrolyte body to heat the solid electrolyte body to a high temperature, and a direct current power source for causing a direct current to flow between said electrodes provided on said solid electrolyte body so as to control oxygen concentration on a side of at least one electrode of said oxygen concentration cell to detect its electromotive force.

Another object of the present invention is to provide an oxygen concentration detector for detecting the oxygen concentration in gases, comprising an oxygen ion conductive solid electrolyte body, at least two separate electrodes contacting the solid electrolyte body so as to form an oxygen concentration cell, said cell having complex impedance characteristics which when graphed exhibit a curve similar to that shown in FIG. 4 hereof, AC power supplying means for applying an AC voltage across said oxygen concentration cell, said AC power supplying means being operable at AC frequencies which is not lower than a frequency which corresponds to its complex impedance characteristics which when graphed in the manner shown in FIG. 4 hereof correspond to point B of said graphed complex impedance characteristic curve, means for affirmatively applying a DC current across said electrodes, said DC current regulating the oxygen concentration in gases, and means for measuring a DC potential difference across said electrodes.

A further object of the present invention is to provide impedance detecting means connected to said electrodes for detecting an impedance of said solid electrolyte.

A still further object of the present invention is to provide the detector wherein at least one of said electrode is embedded in said electrolyte body.

Another object of the present invention is to provide the detector further comprising a refractory material which covers at least one of said electrode.

Another object of the present invention is to provide the detector further comprising means for limiting DC current level through the cell, means for preventing DC current from flowing into the AC power supplying means.

Another object of the present invention is to provide the detector further comprising means for separating a circuit connected to AC power supplying means from the terminal of said oxygen concentration cell.

Another object of the present invention is to provide the detector wherein said AC power supplying means comprises an AC power source and at least one AC electrode separated from said electrodes forming said oxygen concentration cell.

Another object of the present invention is to provide the detector wherein at least a part of said means for affirmatively applying a DC current is a rectifying means for rectifying a part of said AC current into a DC current component.

Another object of the present invention is to provide an oxygen concentration detector for detecting the oxygen concentration in gases comprising an oxygen ion conductive solid electrolyte body, a first set of at least two separate electrodes contacting the solid electrolyte body so as to form an oxygen concentration cell, at least a third electrode separated from the electrodes of said first set, AC power supplying means connected to said third electrode for applying an AC electric voltage through said solid electrolyte body, means for affirmatively applying a DC current across said first set of electrodes and/or said third electrode, said DC current regulating the oxygen concentration in gases, and means for measuring a DC potential difference across electrodes.

Another object of the present invention is to provide the detector further comprising impedance detecting means connected to at least said third electrode for detecting an impedance of said solid electrolyte.

Another object of the present invention is to provide the detector wherein the solid electrolyte body has a tubular shape closed at one end and one of the two separate electrodes is on the inside of the tube and closed end, and the other of the two separate electrodes is on the outside of the tube and closed end.

Another object of the present invention is to provide the detector wherein at least one of said electrode is embedded in said electrolyte body.

Another object of the present invention is to provide the detector further comprising a refractory material which covers at least one of said electrode.

Another object of the present invention is to provide the detector wherein an AC current and an AC voltage between the electrodes have a negative relation, in which when one increases, the other decreases.

Another object of the present invention is to provide a method of detecting oxygen concentration in a gaseous environment using an oxygen concentration cell comprising the steps of providing at least one oxygen concentration cell having at least two separate electrodes contacting an oxygen ion conductive solid electrolyte body, at least one of said electrodes being exposed to gas in a gaseous environment, heating the solid electrolyte body by applying an AC voltage across at least two separate electrodes, and thereby decreasing the impedance of said cell, flowing the DC current across the electrodes which comprises the oxygen concentration cell when said solid electrolyte body is in its heated condition, said DC current regulating the oxygen concentration around at least one of said electrode, and measuring a DC potential difference across said electrodes.

Another object of the present invention is to provide the method further comprising detecting an impedance of the solid electrolyte by the AC voltage applied to the solid electrolyte.

Another object of the present invention is to provide the method wherein at least a part of said DC current are supplied by rectifying a part of AC component.

Another object of the present invention is to provide a method of detecting oxygen concentration in a gaseous environment using an oxygen concentration cell comprising the steps of providing at least one oxygen concentration cell having at least two separate electrodes contacting an oxygen ion conductive solid electrolyte body, at least one of said electrodes being exposed to gas in a gaseous environment, and said cell having a complex impedance characteristic curve similar in shape to that of FIG. 4 hereof, applying an AC voltage across at least two separate electrodes with a frequency such that the cell is operated only at an AC frequency which is not lower than a frequency which corresponds to its complex impedance characteristics which when graphed in the manner shown in FIG. 4 hereof correspond to point B of said graphed complex impedance characteristic curve, flowing the DC current across the electrodes which comprise the oxygen concentration cell when said solid electrolyte body is in its heated condition, said DC current regulating the oxygen concentration around at least one of said electrode, and measuring a DC potential difference across electrodes.

Another object of the present invention is to provide the method further comprising detecting an impedance of the solid electrolyte by the AC voltage applied to the solid electrolyte.

Another object of the present invention is to provide the method wherein the solid electrolyte body is heated to at least about 350° C. by application of the AC voltage across said electrodes.

Another object of the present invention is to provide the method wherein said applied frequency is such that the complex impedance characteristics when graphed in the manner of FIG. 4 hereof corresponds to point C of said graphed complex impedance characteristics.

The AC current and AC voltage between the electrodes are preferably in a negative relation, that is, when one increases, the other decreases. In this case, the AC current preferably has a frequency at which an impedance of an electrostatic capacitance $C_2$ at grain boundaries of the solid electrolyte body is less than a resistance $R_2$ at the grain boundaries, and more preferably has a frequency at which the polarization of the AC current component is caused mainly due to the polarization of the solid electrolyte body caused by a resistance $R_3$ in grains of the body.

In a preferred embodiment of the invention, by applying the alternating current voltage having said frequency the solid electrolyte body is heated and simultaneously the impedance of the body is detected to obtain the temperature of the body.

Moreover, part of the alternating current for heating and/or detecting the impedance may be rectified to obtained the direct current for controlling the oxygen partial pressure.

In order that the invention may be more clearly understood, preferred embodiments will be described, by way of example, with reference to the accompanying drawings.

BRIEF DESCRIPTION OF THE DRAWINGS

FIG. 6 is an explanatory graph illustrating a relation between impedance and temperature of an oxygen concentration cell;

FIG. 7 is an explanatory graph illustrating a relation between vehicle travelled distance and impedance;

DETAILED DESCRIPTION OF THE PREFERRED EMBODIMENT

Figure 1:
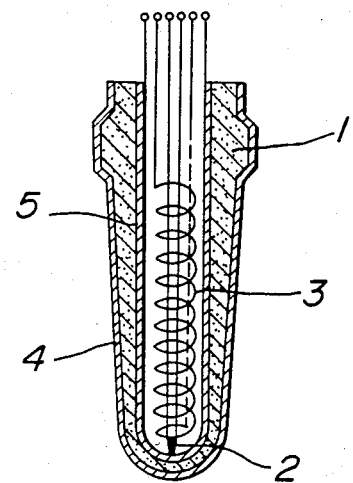
FIG. 1 is an explanatory schematic sectional view of a principal part of the oxygen concentration detector of the prior art as above mentioned.
Figure 2:
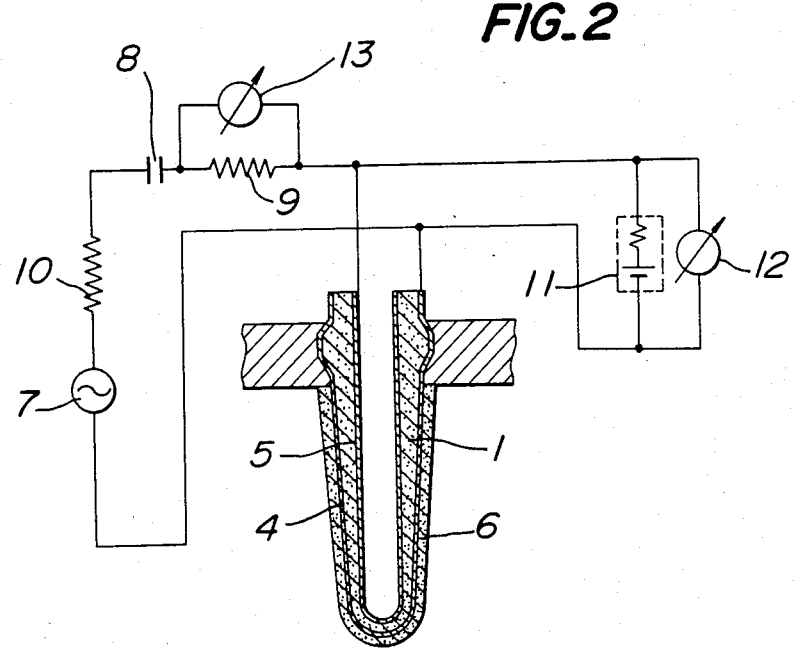
FIG. 2 is a schematic elevation illustrating one embodiment of the oxygen concentration detector according to the invention.

FIG. 2 is an explanatory illustration showing one embodiment of the oxygen concentration detector based on a principle according to the invention. The device comprises a solid electrolyte body 1 in the form of a bottomed cylinder including on its outer and inner surfaces a measured gas electrode 4 and a reference electrode 5. The measured gas electrode 4 is coated with a porous diffusion layer 6. An alternating power source 7 having a frequency at which a polarization of alternating current component is caused mainly due to a polarization of the solid electrolyte body is connected across the measured gas electrode 4 and reference electrode 5 through a direct current component blocking condenser 8, a current detecting resistance 9 and a current restricting resistance 10. Moreover, across the electrodes 4 and 5 are connected in parallel a direct current power source 11 and a direct current voltage detector 12. With such an arrangement, an alternating current is supplied to the solid electrolyte body 1 to effect self-heating and a direct current is supplied to the solid electrolyte body 1 to form a so-called oxygen pump which controls the oxygen concentration on the side of the measured gas electrode 4 to control the air-fuel ratio λ sharply changing the terminal voltage between the electrodes.

Figure 3:
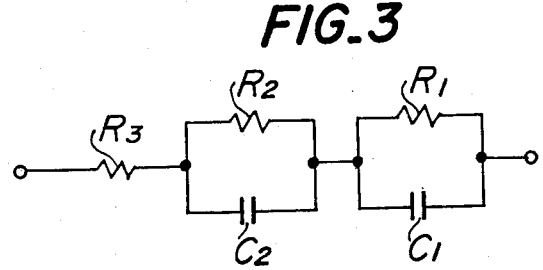
FIG. 3 is an equivalent circuit for an oxygen concentration cell formed in the detector according to the invention.

The self-heating of the solid electrolyte body 1 by applying the AC voltage thereto will be explained. As an oxygen concentration detector for detecting the oxygen concentration of the exhaust gas from an internal combustion engine is required to resist to high temperatures and to exhibit quick response even at low temperatures, a measured gas electrode 4 is made of a metal selected from, for example, the platinum group, which has a large catalytic activity and a high melting point. An equivalent circuit for the oxygen concentration cell is as shown in FIG. 3 which illustrates a polarization resistance $R_1$ at a boundary between the electrode 4 and solid electrolyte body, an electrostatic capacity $C_1$ caused by a polarization at the boundary, a resistance $R_2$ at a boundary of crystals in the solid electrolyte body, an electrostatic capacitance $C_2$ at the boundary of the crystals and a resistance $R_3$ in the crystals of the solid electrolyte body. A frequency characteristic of the impedance of the oxygen concentration cell illustrated in the equivalent circuit is shown as two connected circular arcs in FIG. 4 which indicates it in a complex impedance $Z=Z'-jZ''$. A value at A in FIG. 4 corresponds to $R_1+R_2+R_3$ in FIG. 3, a value at B to $R_2+R_3$ and a value at C to $R_3$. The polarization of the oxygen concentration cell from the point A to point B is mainly based on $R_1$ and $C_1$ and the polarization from B to C is mainly on $R_2$, $R_3$ and $C_2$. The point A corresponds to the direct current. Frequencies become higher from A to B along the arc and much higher from B to C along the arc.

The frequencies of the AC voltage for the self-heating of the solid electrolyte body should be those at which the polarization of AC component is caused mainly due to the polarization of the solid electrolyte body, or within the range from B to C, because it is difficult to supply stably the electric power required for heating owing to great variation in impedance within A to B depending upon attached conditions of the electrodes and due to a long period of used time and it is difficult to supply the power unless the AC voltage is made higher due to the high absolute value of the impedance ten times higher than that from B to C, the high AC voltage causing various disadvantages such as induction trouble from a lead line and bad effect on the electrodes. With the frequencies between A and B, moreover, the boundary between the electrode and solid electrolyte body is subjected to a great voltage so as to cause peeling of the electrode and change in quality of the solid electrolyte body, while the nonlinear polarization characteristic of both the electrodes causes to deviate the direct current so as to affect the DC electromotive force of the oxygen concentration cell resulting into inaccurate oxygen concentration values.

On the other hand, when the AC voltage of the frequency within B to C is applied to the body, it does not cause the peeling of the electrode, change in quality of the solid electrolyte body, and the deviation of the direct current component, even if the current is sufficient to heat the solid electrolyte body, because when AC voltage having a frequency higher than that at B is applied, the most of the polarization is caused in the solid electrolyte body equivalent to $R_2$, $C_2$ and $R_3$, and in the interior of the solid electrolyte body the polarization is uniformly distributed in a direction of the thickness of the body to prevent the decline in quality of the body, while the polarization hardly occurs at the boundary between the electrode and the solid electrolyte body corresponding to $R_1$ and $C_1$ where the decline in quality usually occurs, so that the polarization does not effect on the boundary. In addition, the impedance within the range from B to C is dependent upon a characteristic of the solid electrolyte body itself without depending upon the attached conditions of the electrodes and variation in quality of the body for a long period of used time, so that when an AC voltage having a frequency within the range B to C is applied, the impedance is a low and stable whose value is a fraction or one tenths of the DC resistance with the result that the comparatively low voltage can stably heat the solid electrolyte body. In general, the value $R_1$ rapidly increases in comparison with the values $R_2$ and $R_3$ as the temperature lowers, so that the lowest operating temperature of an oxygen concentration detector is limited. In order to eliminate the effect of $R_1$, according to the invention, the AC voltage having a frequency at which the polarization of AC component is caused mainly due to the polarization of the solid electrolyte body, or the AC voltage within the range from B to C is applied to flow the current in $R_3$ or $R_2$ and $R_3$ owing to the polarization of the solid electrolyte body independent on $R_1$ to heat the body. The AC voltage is applied at a frequency which is sufficiently high that the impedance between the electrodes to which the AC voltage is applied is largely independent of the interface capacitances between those electrodes and the surface of the solid electrolyte body. In this case, the frequency is preferably selected such that the impedance of $C_2$ is less than $R_2$ (FIG. 3) and more preferably the freuquency corresponding to the point C in FIG. 4 causing the polarization by $R_3$. The AC voltage is applied at a frequency which is sufficiently high that the impedance between the electrodes to which AC voltage is applied is largely independent of the intergranular capacitance between crystal grains of the solid electrolyte body.

Moreover, the frequencies in the proximity of the points B and C are not constant depending upon a composition, temperature and shape of the solid electrolyte body and shape of the electrodes. In the case of, for example, a bottomed cylinder as shown in FIG. 2 made of a ceramic material consisting of 100 parts of a mixture including 95 mol % $ZrO_2$ and 5 mol % $Y_2O_3$ and 3 parts of clay, having an external diameter of 3.5 mm at its bottom end, an effective length of 10 mm and a thickness of 0.75 mm and provided on its inner and outer surfaces with platinum electrodes, the frequencies at the points B and C are 10 Hz and 50 KHz at 350° C., respectively.

Figure 5:
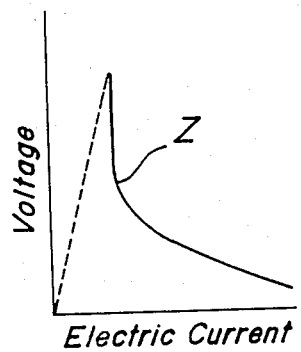
FIG. 5 is an explanatory graph of a voltage-current characteristic when alternating current is applied to a solid electrolyte body.

FIG. 5 illustrates a relation between electric current and voltage when AC voltage within the range from the point B to the point C is applied to the solid electrolyte body, wherein there is a negative relation between the current and voltage, that is one increases, the other decreases, in a zone where the current is more than a determined value (a curve Z). This phenomenon is caused by the fact that when an AC current is applied to a resistance to heat it, the resistor itself exhibits a temperature adjusting performance as explained later with FIG. 12. Accordingly, when a resistance is heated, it is preferable to apply the AC current within the zone of the curve Z because the AC voltage to be applied becomes lower depending upon the self-heating temperature owing to the above negative relation.

The control of the oxygen concentration on the side of the other electrode in connection with the flowing of the direct current will be explained. Referring to FIG. 2, when the direct current source 11 flows the direct current from the reference electrode 5 to the measured gas electrode 4, the oxygen concentration at the boundary between the diffusion layer 6 and the measured gas electrode 4 is controlled by the action of the oxygen pump. In other words, the oxygen in the exhaust gas is diffused into the diffusion layer 6 towards the measured gas electrode 4 at a constant diffusion rate in proportional to a difference between oxygen concentrations on opposite sides of the diffusion layer 6. The diffused oxygen becomes oxygen ion by reaction $O_2 + 4e \rightarrow 2O^{--}$ at the boundary between the measured gas electrode 4 and the solid electrolyte body 1. The oxygen ion then moves in the solid electrolyte body 1 and reaches the reference electrode 5 from which the oxygen ion leaves as oxygen gas. The relation between the oxygen concentration Co in the exhaust gas and the oxygen concentration Ce at the boundary between the measured gas electrode 4 and the solid electrolyte body 1 is indicated by an equation $Ce = Co - KI/nF$, where I is the density of direct current flowing through the measured gas electrode, K is a factor indicating a resistance of the diffusion layer 6 to the diffusion of oxygen, n is an electric change number (in this case, 4) in the reaction of the electrode and F is the Faraday constant. With an oxygen concentration detector utilizing the principle of the oxygen concentration cell, the oxygen concentration Ce at the boundary between the measured gas electrode and solid electrolyte body rapidly changes depending upon a slightly excess of oxygen or fuel in the proximity of zero concentration as can be clear from the Nernst's equation. Accordingly, if K and I in the above equation are selected such that KI/nF equals to Co, the oxygen concentration Ce at the boundary becomes zero at the oxygen concentration Co in any exhaust gas to abruptly change the electromotive force of the oxygen concentration cell. Therefore, the oxygen concentration in an exhaust gas whose air-fuel ratio $\lambda$ is other than 1.0 can be simply detected with high accuracy.

In a further preferred embodiment according to the invention, the electric current flowing through the solid electrolyte body 1 is measured by a current detecting resistance 9 and an AC voltage detector 13 to detect impedance and temperature of the solid electrolyte body 1 as shown in FIG. 2. The detection of the impedance will be explained hereinafter.

Figure 4:
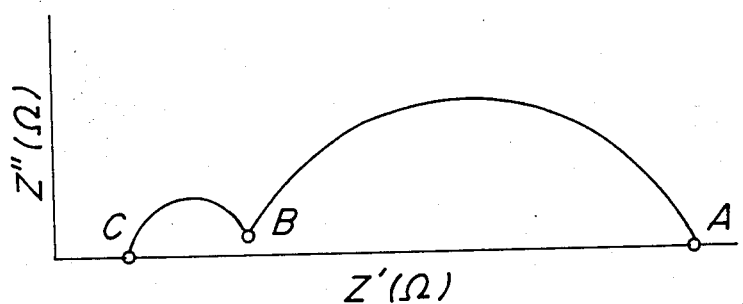
FIG. 4 is an explanatory graph of a complex impedance characteristic of an oxygen concentration cell.

The complex impedance characteristic of the oxygen concentration cell is dependent upon the temperature of the solid electrolyte body such that as the temperature rises, the values at the points A, B and C in FIG. 4 become smaller and the frequencies in the proximity of the points B and C become higher. FIG. 6 illustrates relations between the temperature and impedance when an alternating current having a fixed frequency is applied to the solid electrolyte body. The temperature is determined by the measured impedance of the solid electrolyte body. A curve E in FIG. 6 was obtained with an AC voltage having the frequency corresponding to the point B in FIG. 4 at the temperature $T_2$. A curve F was measured with an AC voltage having the frequency in the vicinity of the point C at the temperature $T_3$. According to the invention the frequency for measuring the impedance is also limited in the same manner as in heating to those at which the polarization of alternating current component is caused mainly due to the polarization of the solid electrolyte body, or the frequencies within the range from the point B to point C or preferably at the point C, because when the temperature rise from $T_2$ to $T_3$ in case of the curve E in FIG. 6, the impedance varies from the point B to the point A along the arc within which range the impedance is greatly influenced by the conditions of the boundary between the electrode and solid electrolyte body and attached conditions of the electrodes and is very unstable after a long period of used time.

Moreover, within the frequency range corresponding to between the points B and C wherein polarization of AC component is caused mainly due to the polarization of the solid electrolyte body, the impedance does not vary unless the crystals of the solid electrolyte body and boundaries between the crystal grains. Accordingly, the impedance is very stable for a long period of time. The frequencies in the proximity of the point C is more preferable as can be seen from FIG. 7 illustrating change percentage in impedance of the oxygen concentration detector at 400° C. versus travelling distances of a vehicle. Curves G, H, J and K were measured with the direct current corresponding to point A, with a frequency at a substantially intermediate point on the arc between points A and B, with a frequency in the proximity of point B and with a frequency in the proximity of point C, respectively. The curves J and K illustrate the fact that within the frequency range in which the polarization of AC component is caused mainly due to the polarization of the solid electrolyte body, the impedance is very stable for a long period of time.

According to the invention, moreover, as the temperature of the solid electrolyte body is detected with the aid of the impedance of the body, the actual temperature can be precisely obtained without any time delay.

Figure 8:
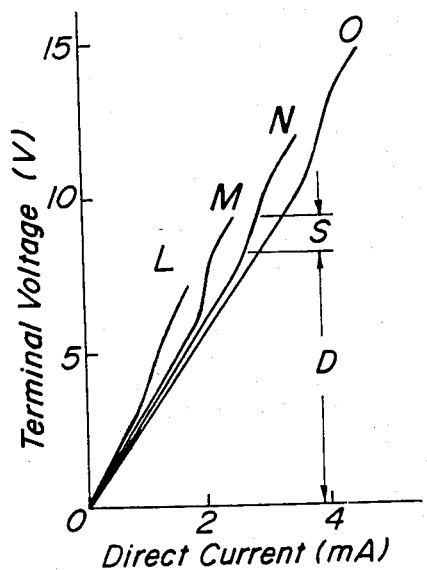
FIGS. 8 and 9 are explanatory graphs illustrating relations between terminal voltage and direct current and air-fuel ratio when direct current flows in an oxygen concentration cell of the prior art, respectively.
Figure 9:
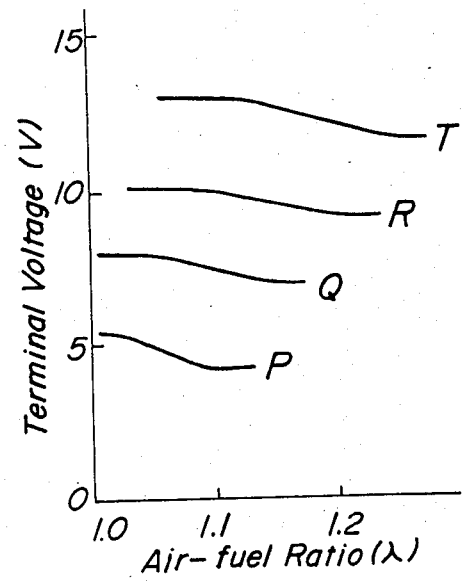
Figure 10:
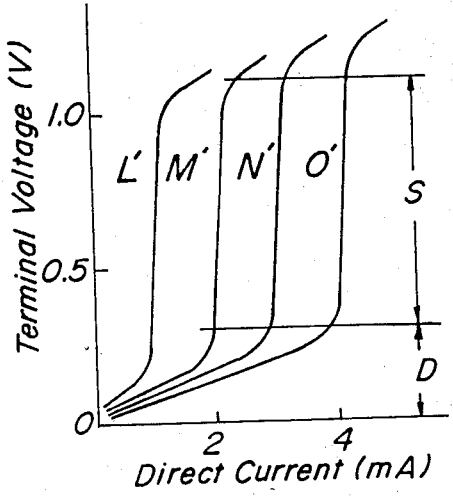
FIGS. 10 and 11 are explanatory graphs similar to FIGS. 8 and 9 but when direct current flows in the oxygen concentration cell according to the invention, respectively.
Figure 11:
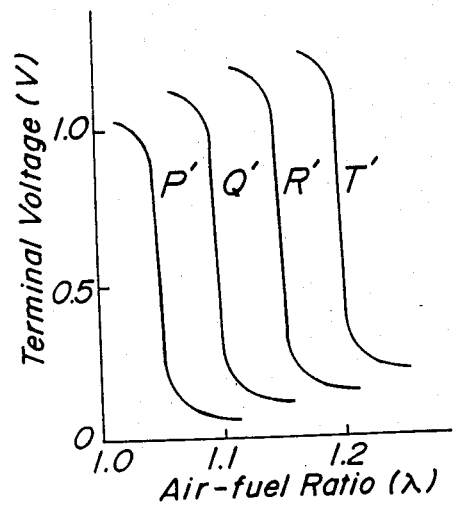

According to the invention, as the direct current flows through the solid electrolyte body which is in heated condition by applying the alternating current, the polarization of the oxygen concentration cell caused by the direct current is very small which is negligible relative to the electromotive force of the oxygen concentration cell, even if the exhaust gas is at a low temperature. FIGS. 8-11 illustrate terminal voltages of the oxygen concentration cell when the exhaust gas is approximately at 450° C. FIGS. 8 and 9 illustrate relations between the current and voltage and between the air-fuel ratio and voltage of a prior art oxygen concentration cell without heating, respectively. FIGS. 10 and 11 show relations between the current and voltage and between the air-fuel ratio and voltage of the oxygen concentration cell self-heated by applying the AC voltage according to the invention. In more detail, FIGS. 8 and 10 illustrate the relations between the direct current and terminal voltage of the oxygen concentration cells in curves L, M, N and O and L', M', N' and O' when the oxygen concentration in the exhaust gas is 1, 2, 3 and 4%, respectively, and FIGS. 9 and 11 illustrate the relations between the air-fuel ratio $\lambda$ and terminal voltage (V) of the oxygen concentration cells in curves P, Q, R and T and P', Q', R' and T' when the direct current is 1, 2, 3 and 4 mA, respectively. In this case, when the air-fuel ratio $\lambda$ is 1.1, the oxygen concentration in the exhaust gas is about 2% and when the ratio $\lambda$ is 1.2, the concentration is about 4%. As can be seen from FIGS. 8 and 10, the terminal voltage of the oxygen concentration cell greatly increases stepwise at a value, as the direct current is increased, and the sharply increased voltage (shown by S in FIGS. 8 and 10) is about 1 V independent on heating, which substantially corresponds to the electromotive force of the oxygen concentration cell. The value of the direct current at which the terminal voltage starts to sharply increase is determined by the oxygen concentration in the exhaust gas and construction of the diffusion layer. For example, when the oxygen concentration is 2%, the direct current at which the terminal voltage starts to sharply vary is 2 mA as shown by the curves M and M' in FIGS. 8 and 10. In FIG. 8 which concerns the prior art oxygen concentration detector without heating, the stepwise increase S is about 1 V but the polarization D owing to the direct current flowing through the oxygen concentration cell is comparatively large such as several to ten and a few V. The value D is greatly changed depending upon the temperature of the exhaust gas, so that it is difficult to detect the air-fuel ratio $\lambda$ by the terminal voltage which is a sum of the stepwise variation S caused by the electromotive force of the oxygen concentration cell and the polarization D resulting from the direct current. In the condition of such a large polarization, peeling of electrodes and change in quality of the solid electrolyte body are apt to occur, so that the detector could not be used for long time. In contrast herewith, with the oxygen concentration detector with heating according to the invention as shown in FIG. 10, the stepwise increase of the terminal voltage is about 1 V which is substantially equal to the value in the prior art but the polarization D owing to the direct current through the oxygen concentration cell is only 0.2–0.3 V which is not affected by the temperature of the exhaust gas and is negligible relative to the value S resulting from the electromotive force. Moreover, the flowing of the direct current does not affect the electrodes and solid electrolyte body. Therefore, as viewed in the characteristic curves illustrating relations between the terminal voltage and the air-fuel ratio $\lambda$ in FIG. 11, with the oxygen concentration detector with heating according to the invention, the stepwise increase in terminal voltage occurs within the range from about 0.3 V to 1 V, so that the air-fuel ratio $\lambda$ can be easily controlled with high accuracy employing the terminal voltage 0.6 V as a reference value.

Figure 12:
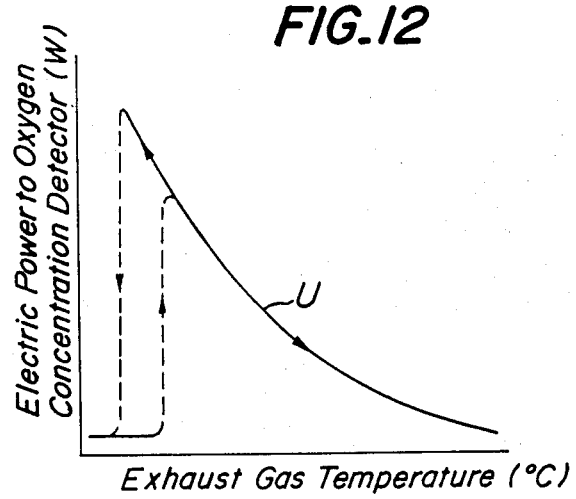
FIG. 12 is a graph for explaining a temperature self-controlling performance of the oxygen concentration detector according to the invention.
Figure 13:
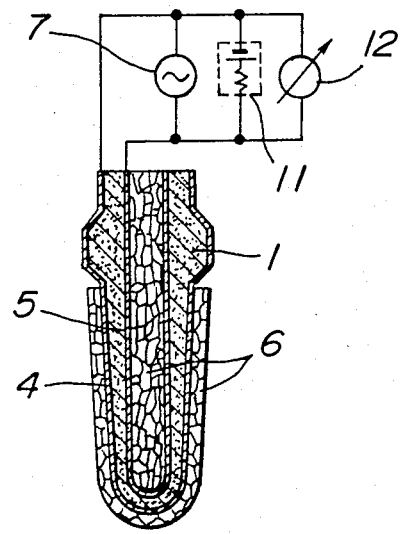
FIG. 13 is a schematic elevation illustrating another embodiment of the oxygen concentration detector according to the invention.

The current restricting resistance 10 in FIG. 2 prevents excess current from flowing through the oxygen concentration cell and serves to lower the electric power applied to the oxygen concentration cell at a high temperature at which heating is not required. A curve V in FIG. 12 illustrates relations between temperatures of gases to be measured by the oxygen concentration detector shown in FIG. 2 and electric power to be applied to the solid electrolyte body 1. This relation gives the solid electrolyte body itself a temperature controlling performance within the negative characteristic zone, so that the change in electromotive force due to change in temperature of gases to be measured is small and the change in diffusion rate in the diffusion layer 6 can be also restrained to a very small value to improve the accuracy of the oxygen concentration detector. In FIG. 2, the current restricting resistance 10 and the current detecting resistance 9 for detecting impedance may be a capacitor or an inductor. And the resistor, inductor and capacitor for restricting current and for detecting current may be commonly used. Although the direct current blocking capacitor 8 is for blocking the direct current component from the AC source 7 to the oxygen concentration cell, the capacitor 8 may be commonly used for detecting and restricting current, and one capacitor may be used for all the purposes.

The diffusion layer 6 may be additionally provided on the side of the reference electrode 5. In this case, when the air-fuel ratio λ at the sharp change in electromotive force by flowing the direct current is controlled, the oxygen in the gas to be measured is simultaneously carried into the diffusion layer 6, so that the layer 6 serves as a reference of approximately 1 atom oxygen partial pressure for the oxygen concentration cell. Accordingly, the reference electrode 5 need not communicate with the atmosphere, so that it becomes simple in construction and is small sized. Moreover, the diffusion layer 6 may be an equivalent to a protective layer of spinel or the like provided for protecting the measured gas electrode 4 from the gas to be measured.

Although the current detecting resistance 9 is for measuring the impedance of the oxygen concentration cell to detect the temperature of the solid electrolyte body 1, the voltage or the like of the AC source 7 can be controlled with the aid of the voltages or the like at the ends of the resistance 9 to maintain constant the temperature of the solid electrolyte body 1. The impedance may be measured by the AC voltage across the current restricting resistance 10 or between the electrodes of the solid electrolyte body other than the above.

Figure 14:
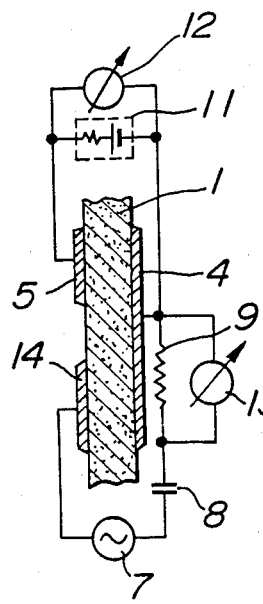
FIGS. 14–18 explanatorily illustrate various connections of electrodes to the oxygen concentration cell of the oxygen concentration detector according to the invention.
Figure 15:
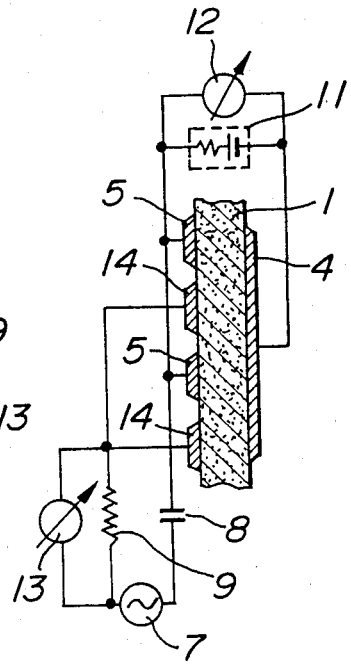
Figure 17:
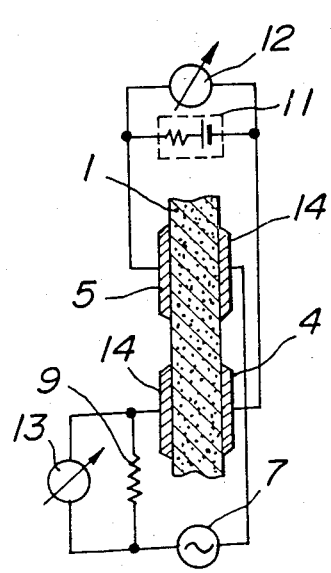
Figure 18:
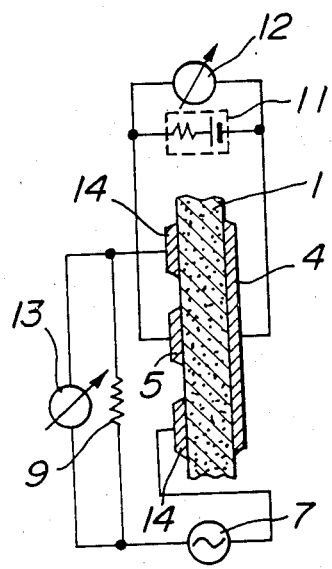

An AC source for detecting the impedance and an AC source for heating may be provided separately and may be different in frequency. The electrode to be provided on the solid electrolyte body for applying the AC may be used commonly to the measured gas electrode 4 for the oxygen concentration cell and reference electrode 5 shown in FIG. 2. Moreover, as shown in FIGS. 14 and 15, only an AC voltage applying electrode or electrodes 14 may be independently provided and may be used commonly to the other electrodes, or as shown in FIGS. 17 and 18, respectively independent AC voltage applying electrodes may be provided. Furthermore, AC voltage applying electrodes may be independently provided for detecting the impedance and for heating the body.

In addition, it is preferable to obtain the direct current for controlling the partial oxygen pressure at the electrode by rectifying the alternating current for heating and/or detecting the impedance, because only one power source can supply all the required current to lower the cost.

Figure 16:
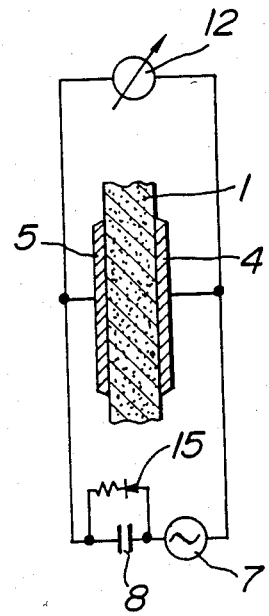

The application of AC voltage, flowing of direct current and detection of impedance and electromotive force may be always or continuously effected (i.e. simultaneously) or may be effected by time sharing system with the aid of switching circuits or the like. The direct current may be caused to flow by rectifying part of the alternating current as shown in FIG. 16. In order to prevent the AC voltage from flowing into a DC voltage detector 12, a filter circuit may be used which has been known as the LC circuit, RC circuit or the like.

The solid electrolyte body used for the oxygen concentration detector according to the invention may be the bottomed cylinder as shown in FIG. 2 or plate-like as shown in FIGS. 14–18 or a thin film (not shown). The part of the body to be heated may be formed thinner than the remaining part, or as shown in FIGS. 14–18 the electrodes may be provided only on the parts to be heated, thereby enabling the heating portion to be determined. Therefore, the thickness of the diffusion layer 6 is made uniform only over the heating portion to make the change in electromotive force abrupt. In the prior art, when the diffusion layer is not uniform in thickness, the diffusion rate of the oxygen becomes uneven or uniform, with the result that there are differences in sharply changing electromotive force between the thick and thin portions to lose the sharply change in electromotive force as a whole. However, if the solid electrolyte body is partially heated, only the partially heated portion serves mainly as an oxygen concentration cell, so that all that is required is to make uniform the thickness of the diffusion layer at the heated portion. It is preferable that the diffusion layer at the portion not heated is made thicker or the electrode at the portion not heated is covered with an air-tight layer. According to the invention, moreover, in the event of partial or local heating, actual temperatures at which the solid electrolyte body actuates are obtained with high accuracy because the impedance is detected for measuring the temperatures.

The solid electrolyte body to be heated has a negative temperature coefficient, so that it is often impossible to flow sufficient current for heating because of high resistance at low temperatures. In this case, it is preferable to preheat the body to a temperature permitting sufficient electric current to flow therethrough by embedding a auxiliary heater in the solid electrolyte body or arranging the heater in the proximity of the resistor.

Examples of the detector according to the invention will be explained hereinafter.

EXAMPLE 1

Figure 19:
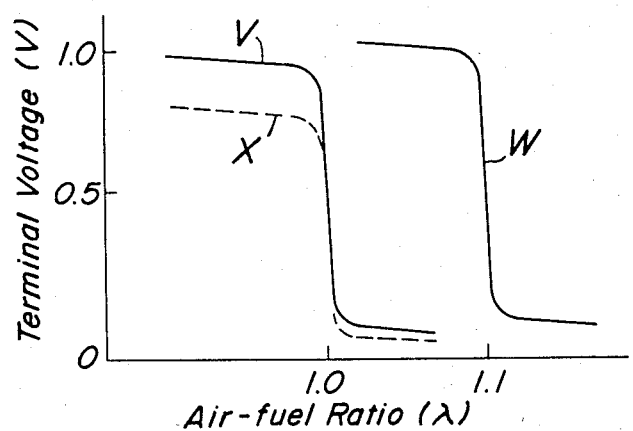
FIGS. 19 and 20 are graphs for explaining results of experiments on embodiments of the oxygen concentration detector according to the invention.

A solid electrolyte body in the form of a bottomed cylinder was made of a zirconia ceramics consisting of 100 parts by weight of a mixture including 95 mol % $ZrO_2$ and 5 mol % $Y_2O_3$ and 3 parts by weight of a clay and had at its front end 3.5 mm outer diameter and 2 mm inner diameter and at its intermediate portion 5 mm outer diameter and 2.5 mm inner diameter. The solid electrolyte body was provided on its outer and inner surfaces with a measured gas electrode 4 and a reference electrode 5 of platinum and was coated on its outer surface with a diffusion layer 6 of porous spinel having a thickness of 0.5 mm to form an oxygen concentration detector. Between the electrodes 4 and 5 was connected an AC voltage source of 70 V and 50 KHz frequency through a DC component blocking capacitor 8 and a current restricting resistor 10 of 200Ω. The oxygen concentration detector was arranged in the exhaust gas of an engine whose air-fuel ratio was known and a direct current was caused to flow from the reference electrode 5 to the measured gas electrode 4. Terminal voltages (V) of the detector were measured with the air-fuel ratio λ being progressively changed. The results are shown in FIG. 19 wherein a dashed line X illustreates results of the prior art without heating and solid lines V and W show results of the detector with heating according to the invention. With the line W, 2 mA direct current was caused to flow, but with the lines V and X no direct current. The temperature of the measured gas was 250° C. As can be seen from FIG. 19, the terminal voltages change sharply even in the line W the direct current flowed according to the invention. In contrast herewith, with the prior art detector flowing the direct current and without heating, the terminal voltage was more than 150 V and did not exhibit any sharp change (not shown).

Next, the temperature of the measured gas was progressively raised from 250° C. and voltage across the current restricting resistor 10 was measured to obtain impedance of the solid electrolyte body. The temperature was obtained from the relation between the impedance and temperature. In this case, the air-fuel ratio λ of the measured gas was 1.0 and direct current was 2 mA. The results are shown in Table 1. From the Table 1, although the temperatures of the gas changed from 250° C. to 650° C., the actually measured temperature at the end of the oxygen concentration detector according to the invention varied only within the range of about 500° C. to 680° C. (while the electric power to the solid electrolyte body was changed from 3.8 W to 0.4 W) to exhibit a function keeping the element or detector at a constant temperature. Moreover, the temperatures of the element obtained from the impedance are very close to the actually measured temperatures at the end of the element. This fact means that the actual temperature of the element can be obtained by the detection of the impedance.

TABLE 1

| Temperature of measured gas (°C.) | Impedance of solid electrolyte body (Ω) | Temperature from impedance (°C.) | Actually measured temperature at end of detector (°C.) | Electric power applied to solid electrolyte body (W) | Air-fuel ratio causing electromotive force to change sharply (λ) |
| --- | --- | --- | --- | --- | --- |
| 250 | 47 | 500 | 503 | 3.8 | 1.11 |
| 350 | 28 | 530 | 532 | 2.6 | 1.10 |
| 450 | 16 | 560 | 561 | 1.7 | 1.11 |
| 550 | 8  | 610 | 609 | 0.9 | 1.09 |
| 650 | 3  | 680 | 682 | 0.4 | 1.10 |

Moreover, response time of the oxygen concentration detector were measured with and without the flow of direct current at the temperatures 250° C., 350° C. and 450° C. of the measured gas. As can be seen from Table 2 showing the results, the response time of the detector according to the invention was very high in comparison with reference detectors. With detectors with direct current flowing therethrough without heating, the terminal voltages were too high to measure the response time.

TABLE 2

| | Heating | Direct current | Measured gas temperature (°C.) | Response time (Sec) |
| --- | --- | --- | --- | --- |
| Detector according to the invention | yes | yes | 250 | 0.12 |
|  |  |  | 300 | 0.12 |
|  |  |  | 350 | 0.09 |
|  |  |  | 400 | 0.09 |
| Reference detector of prior art | yes | no | 250 | 0.13 |
|  |  |  | 300 | 0.12 |
|  |  |  | 350 | 0.12 |
|  |  |  | 400 | 0.09 |
|  | no | yes | 250 |  |
|  |  |  | 300 | impossible to measure |
|  |  |  | 350 |  |
|  |  |  | 400 |  |
|  | no | no | 250 | 2.85 |
|  |  |  | 300 | 1.29 |
|  |  |  | 350 | 0.36 |
|  |  |  | 400 | 0.18 |

Note:
The response time is indicated by the time required for the terminal voltage to change from 0.6 V to 0.3 V when the excess-air ratio λ is changed from 1.0 to 1.2 with the flowing of direct current and from 0.9 to 1.1 without the direct current.

Figure 20:
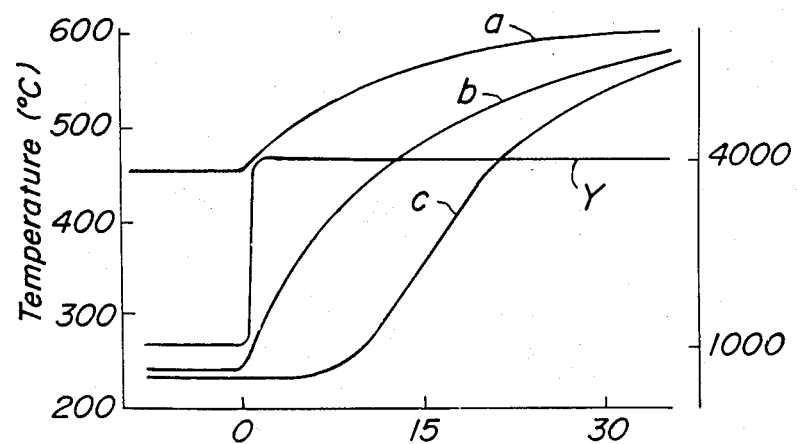

Furthermore, the variation in temperature of the solid electrolyte body was measured from the variation in impedance of the oxygen concentration detector when the rotating speed of the engine was rapidly increased from 1,000 rpm to 4,000 rpm with the excess-air ratio 1.1 in the exhaust gas system of the engine and the flowing of direct current. For the purpose of comparing with the prior art, the temperature was measured by the temperature sensor arranged in the bottomed cylindrical oxygen concentration detector of the prior art. Results are illustrated in FIG. 20, wherein a curve Y shows the change in engine revolution, a curve a of variation in temperature of the solid electrolyte body obtained by impedance according to the invention, a curve b of variation in exhaust gas temperature and c of variation in temperature of the solid electrolyte body obtained by the prior art temperature sensor. As can be seen from FIG. 20, when the engine revolution rapidly increases, the exhaust gas temperature and also solid electrolyte body temperature rise and the temperature of the oxygen concentration cell as shown in the line a rises correspondingly to the solid electrolyte body temperature. In this case, the curve a illustrating the temperature variation of the solid electrolyte body obtained by the impedance according to the invention quickly follows the curve b illustrating the variation in exhaust gas temperature. On the other hand, the curve c of the prior art oxygen concentration detector considerably lags behind the curve b to detect the temperature and therefore when the exhaust gas temperature is changed, the correction of electromotive force and correction of diffusion rate with respect to temperature were clearly inaccurate.

EXAMPLE 2

Figure 21:
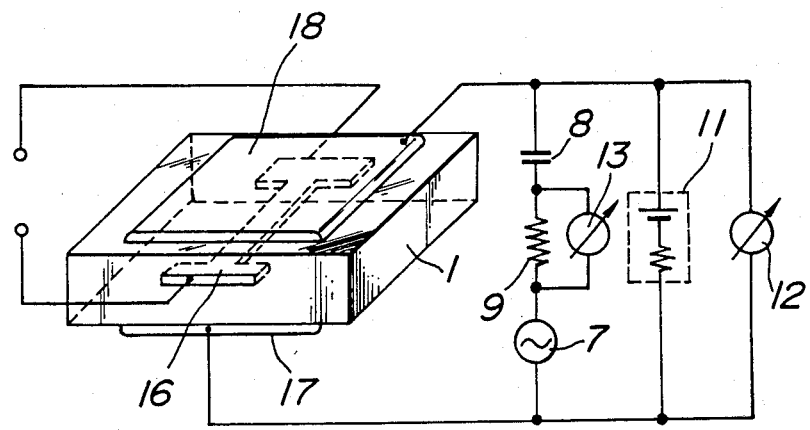
FIG. 21 is an explanatory elevation of the oxygen concentration detector with a supplementary heater according to the invention.

As shown in FIG. 21, a plate-like solid electrolyte body 1 having a width 5 mm, length 8 mm and thickness 0.7 mm was made of the zirconia ceramic having the same composition as that of Example 1. A auxiliary heater 16 of tungsten was embedded in the plate-like solid electrolyte body 1 and independent electrodes 17 and 18 were provided on respective surfaces of the body. The electrodes 17 and 18 were coated with porous spinel layers having thickness 0.5 mm and 1 mm, respectively, to complete the oxygen concentration element. Between the electrodes 17 and 18 was connected an AC voltage source of 50 V. and 100 KHz frequency through a direct current blocking capacitor 8 serving also a current restricting resistor and a current detecting resistor 9 in parallel with an AC voltage detector 13, and a DC source 11 and a DC voltage detector 12 in parallel therewith were connected so as to cause direct current to flow from the electrode 18 to the electrode 17 to complete the oxygen concentration detector. The oxygen concentration detector was arranged in the exahust gas at 20° C. and current was caused to flow through the auxiliary heater 16 as second heating means to preheat the solid electrolyte body 1 to about 350° C. Thereafter, the AC source 7 as first heating means was actuated to supply current to the solid electrolyte body resulting in self-heating and then the heating by the auxiliary heater 16 as the second heating means was stopped. As a result of this the temperature of the solid electrolyte body was maintained by the self-heating at a substantially constant temperature, which was 720° C. actually measured and 730° C. obtained from the detection of the impedance. The direct current from the electrodes 18 to 17 by the DC source 11 was 6 mA. In this condition, while the air-fuel ratio λ was progressively changed, the voltage between the electrodes of the oxygen concentration detector element was measured to find an abrupt electric voltage change at λ=1.15.

EXAMPLE 3

Figure 22:
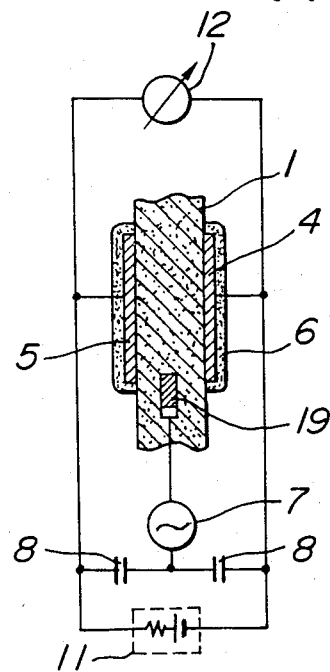
FIG. 22 is a schematic elevation illustrating another embodiment of the oxygen concentration detector having an embedded electrode and an electrode covered with a refractory material according to the present invention.

As shown in FIG. 22, a plate-like solid electrolyte body 1 having a width 5 mm, length 8 mm and thickness 0.7 mm was made of the zirconia ceramic having the same composition as that of Example 1. A electrode 19 of platinum was embedded in the plate-like solid electrolyte body 1 and independent electrodes 4 and 5 were provided on respective surfaces of the body. The electrodes 4 and 5 were covered with porous refractory material layers such as spinel layers having thickness 0.5 mm and 1 mm, respectively, to complete the oxygen concentration element. Between said embedded electrode 19 and the electrodes 4 and 5, respectively was connected an AC voltage source 7 of 50 V and 100 KHz frequency through a direct current blocking capacitor 8 serving also a current restricting resistor and a DC source 11 and a DC voltage detector 12 in parallel therewith were connected so as to cause direct current to flow from the electrode 5 to the electrode 4 to complete the oxygen concentration detector. The oxygen concentration detector was arranged in the exhaust gas at about 350° C. The AC source 7 was actuated to supply current to the solid electrolyte body 1 resulting in self-heating. As a result of this the temperature of the solid electrolyte body 1 was maintained by the self-heating at a substantially constant temperature, which was 720° C. actually measured. The direct current from the electrodes 5 to 4 by the DC source 11 was 6 mA. In this condition, while the air-fuel ratio λ was progressively changed, the voltage between the electrodes of the oxygen concentration detector element was measured to find an abrupt electric voltage change at λ=1.15.

In this example, one electrode 19 for applying AC current is embedded and the electrode 4 which is disclosed in gases was covered by refractory material layer 6 such as spinel layer. Therefore, the deterioration of those electrodes 4, 5 and 19 had not been caused and the correct value was detected and the long life of those electrodes 4, 5 and 19 can be expected.

As above explained in detail, the oxygen concentration detector according to the invention comprises electrodes provided on the solid electrolyte body constituting an oxygen concentration cell to which electrodes is applied an AC voltage of a frequency at which the polarization of AC component is caused mainly due to the polarization of the solid electrolyte body to heat it by its self-heating, and a DC source causing direct current to flow from one electrode to the other electrode of the solid electrolyte body to control the oxygen concentration on the side of one electrode, and preferably to detect the impedance of the solid electrolyte body. With this arrangement, there is no deviation of direct current between the electrodes, notwithstanding the comparatively low voltage and the heating is stably effected independently upon the attached condition of the electrodes to the body for long time. As the solid electrolyte body itself is heated, only small electric power is required. Even if the direct current flows, the air-fuel ratio λ causing the electromotive force to change sharply can be controlled at the low terminal voltage of the oxygen concentration cell. Furthermore, as the oxygen concentration on the side of the reference electrode is controlled by the flow of direct current, it is possible to constitute the reference electrode so as not to communicate with the atmosphere. The detector according to the invention can detect the temperature of the solid electrolyte body exactly and stably without any time delay for long use. As the partial or local heating is easily carried out according to the invention, it is sufficient to make uniform in thickness the diffusion layer only at the heated portion in order to obtain the abrupt change in electromotive force. Moreover, as the self-heating of the solid electrolyte body implies the temperature self-controlling performance, the oxygen concentration detector according to the invention is superior in accuracy, responsibility and service life, resulting from the fact that the change in diffusion rate due to variation in temperature of the diffusion layer is little and the change in air-fuel ratio λ causing the sharp change in electromotive force due to the change in diffusion rate is also little. The detector according to the invention is advantageously simple in construction because it does not require a temperature detecting element and a heating wire which are essential for the prior art detector. The oxygen concentration detector according to the invention is very useful to control an internal combustion engine so as to bring its air-fuel ratio into a lean or rich burn zone and is a beneficial detector for industries.

It is further understood by those skilled in the art that the foregoing description is that of preferred embodiments of the disclosed detectors and that various changes and modifications may be made in the invention without departing from the spirit and scope thereof.

What is claimed is:

1. An oxygen concentration detector for detecting the oxygen concentration in gases, comprising:
   an oxygen ion conductive solid electrolyte body;
   a plurality of separate electrodes contacting the solid electrolyte body, at least two of said plurality of separate electrodes having the solid electrolyte body therebetween, thereby forming an oxygen concentration cell for detecting oxygen partial pressure in a gas;
   AC power supplying means connected to at least two of said plurality of separate electrodes having the solid elctrolyte body therebetween, for applying an AC voltage across said solid electrolyte body through said electrodes, said AC power supplying means being arranged to supply an AC voltage at a frequency sufficiently high such that an impedance between said electrodes to which AC voltage is applied is largely independent of interface capacitances between said electrodes to which AC voltage is applied and a surface where said separate electrodes contact said solid electrolyte body;
   means for simultaneously applying a DC current across said electrodes, said DC current regulating the oxygen concentration in gases; and
   electromotive force detecting means connected to at least two of said plurality of separate electrodes having the solid electrolyte body therebetween, for detecting an electromotive force of the oxygen concentration cell.

2. The detector of claim 1 further comprising:
impedance detecting means connected to at least two of said plurality of separate electrodes having the solid electrolyte body therebetween, for detecting an impedance of said solid electrolyte body.

3. The detector of claim 1 or 2 wherein at least one electrode of said at least two electrodes is embedded in said electrolyte body.

4. The detector of claim 1 or 2 further comprising a refractory material which covers at least one electrode of said at least two electrodes.

5. The detector of claim 1 or 2 further comprising means for limiting DC current level through the cell and means for preventing DC current from flowing into the AC power supplying means.

6. The detector of claim 1 or 2 further comprising means for separating a circuit connected to AC power supplying means from a terminal of said oxygen concentration cell.

7. The detector of claim 1 or 2 wherein said AC power supplying means comprises an AC power source and at least one other electrode separate from said at least two electrodes forming said oxygen concentration cell.

8. The detector of claim 1 or 2 wherein at least a part of said means for simultaneously applying a DC current is a rectifying means for rectifying a part of said AC current into a DC current component.

9. An oxygen concentration detector for detecting the oxygen concentration in gases, comprising:
an oxygen ion conductive solid electrolyte body;
a first set of at least two separate electrodes contacting the solid electrolyte body and having said solid electrolyte body therebetween, thereby forming an oxygen concentration cell;
at least a third electrode separate from the electrodes of said first set;
AC power supplying means connected to said at least a third electrode and at least one of said at least two separate electrodes, said at least a third electrode and said at least one of said at least two separate electrodes having the solid electrolyte body therebetween, for applying an AC electric voltage through said solid electrolyte body, said AC power supplying means being arranged to supply an AC voltage at a frequency sufficiently high that an impedance between said electrodes to which AC voltage is applied is largely independent of interface capacitances between said electrodes to which AC voltage is applied and a surface where said electrodes contact said solid electrolyte body;
means for simultaneously applying a DC current across at least two electrodes selected from the group consisting of said first set of electrodes and said at least a third electrode, said DC current regulating the oxygen concentration in gases; and
electromotive force detecting means connected to at least two of said plurality of separate electrodes having the solid electrolyte body therebetween, for detecting an electromotive force of the oxygen concentration detector.

10. The detector of claim 9 further comprising:
impedance detecting means connected to at least said third electrode and one of said first set of at least two separate electrodes for detecting an impedance of said solid electrolyte.

11. The detector of claim 1, 2, 9 or 10 wherein the solid electrolyte body has a tubular shape having an inside and an outside, the tube being closed at one end and one of said at least two separate electrodes is on the inside of the tube and adjacent the closed end, and another of said at least two separate electrodes is on the outside of the tube and adjacent the closed end.

12. The detector of claim 9 or 10 wherein at least one of said electrodes is embedded in said electrolyte body.

13. The detector of claim 9 or 10 further comprising a refractory material which covers at least one of said electrodes.

14. The detector of claim 1, 2, 9 or 10 wherein an AC current and an AC voltage between the electrodes have a negative relation, wherein when one increases, the other decreases.

15. A method of detecting oxygen concentration in a gaseous environment using an oxygen concentration cell comprising the steps of:
providing at least one oxygen concentration cell having at least two separate electrodes contacting an oxygen ion conductive solid electrolyte body, said at least two separate electrodes having the solid electrolyte body therebetween, at least one of said electrodes being exposed to gas in a gaseous environment;
heating the solid electrolyte body by supplying an AC voltage across at least two separate electrodes, said at least two separate electrodes having the solid electrolyte body therebetween, said AC voltage being supplied at a frequency sufficiently high such that an impedance between said electrodes to which AC voltage is applied is largely independent of interface capacitances between said electrodes to which AC voltage is applied and a surface where said separate electrodes contact said solid electrolyte body, thereby decreasing the impedance of said cell;
flowing the DC current across the electrodes which comprise the oxygen concentration cell when said solid electrolyte body is in its heated condition, said DC current regulating the oxygen concentration around at least one of said electrodes; and
measuring a DC potential difference across said electrodes.

16. The method of claim 15, further comprising:
detecting an impedance of the solid electrolyte resulting from the AC voltage applied to the solid electrolyte.

17. The method of claim 15 or 16, wherein at least a part of said DC current is supplied by rectifying a part of the AC component.

18. A method of detecting oxygen concentration in a gaseous environment using an oxygen concentration cell comprising the steps of:
providing at least one oxygen concentration cell having at least two separate electrodes contacting an oxygen ion conductive solid electrolyte body, said at least two separate electrodes having the solid electrolyte body therebetween, at least one of said electrodes being exposed to gas in a gaseous environment;
applying an AC voltage across said electrolyte body through at least two separate electrodes having the solid electrolyte body therebetween, with a frequency such that the cell is operated only at an AC frequency sufficiently high such that an impedance between said electrodes to which AC voltage is applied is largely independent of interface capacitances between said electrodes to which AC voltage is applied and a surface where said separate electrodes contact said solid electrolyte body;

flowing a DC current across said at least two electrodes comprising the oxygen concentration cell when said solid electrolyte body is in its heated condition, said DC current regulating the oxygen concentration around at least one of said at least two electrodes;

measuring a DC potential difference across said at least two electrodes.

19. The method of claim 18 further comprising:

detecting an impedance of the solid electrolyte resulting from the AC voltage applied to the solid electrolyte.

20. The method of claim 18 or 19 wherein the solid electrolyte body is heated to at least about 350° C. by application of the AC voltage across said electrodes.

21. The method of claim 18 or 19 wherein said applied frequency is sufficiently high such that the impedance between said electrodes to which AC voltage is applied is largely independent of intergranular capacitances between crystal grains of said solid electrolyte body.

* * * * *